US00PP32483P3

(12) United States Plant Patent
Hoogkamp

(10) Patent No.: US PP32,483 P3
(45) Date of Patent: Nov. 17, 2020

(54) ***SPATHIPHYLLUM* PLANT NAMED 'SPAMALGRO'**

(50) Latin Name: ***Spathiphyllum* Schott.**
Varietal Denomination: Spamalgro

(71) Applicant: Timothy Johan Herman Hoogkamp, Doetinchem (NL)

(72) Inventor: Timothy Johan Herman Hoogkamp, Doetinchem (NL)

(73) Assignee: NUBILUS B.V., Naaldwijk (NL)

( * ) Notice: Subject to any disclaimer, the term of this patent is extended or adjusted under 35 U.S.C. 154(b) by 0 days.

(21) Appl. No.: 16/602,990

(22) Filed: Jan. 11, 2020

(65) Prior Publication Data

US 2020/0229335 P1 Jul. 16, 2020

Related U.S. Application Data

(60) Provisional application No. 62/918,087, filed on Jan. 12, 2019.

(51) Int. Cl.
*A01H 5/02* (2018.01)
*A01H 6/10* (2018.01)
*A01H 6/00* (2018.01)

(52) U.S. Cl.
USPC ..... Plt./364
CPC ..... *A01H 6/00* (2018.05); *A01H 5/02* (2013.01)

(58) Field of Classification Search
USPC ..... Plt./263.1, 364
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Spathiphyllum* plant named 'Spamalgro', characterized by its large, upright, outwardly arching and uniform plant habit; freely clumping growth habit; bushy and dense plants; large glossy dark green-colored leaves; freely flowering habit; large white-colored spathes that are positioned between and above the foliar plane on strong and erect scapes; flowers that produce very little to no pollen; and good inflorescence longevity.

3 Drawing Sheets

Figure 1:
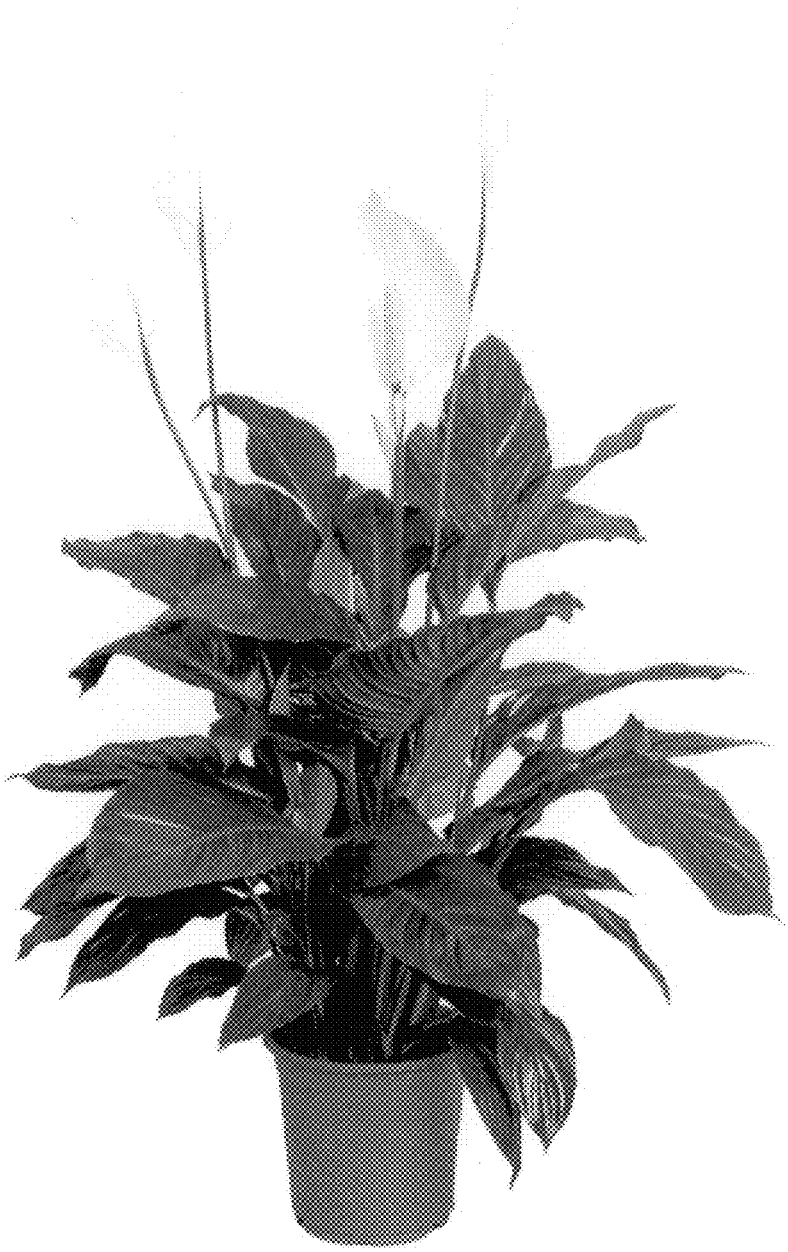

Botanical designation: *Spathiphyllum* Schott.
Cultivar denomination: 'SPAMALGRO'.

BACKGROUND OF THE INVENTION

The present invention relates to a new and distinct cultivar of *Spathiphyllum* plant, botanically known as *Spathiphyllum* Schott. and hereinafter referred to by the cultivar name 'Spamalgro'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in October, 2012 of a proprietary selection of *Spathiphyllum* Schott. identified as code number 20081932-45, not patented, as the female, or seed, parent with a proprietary selection of *Spathiphyllum* Schott. identified as code number 20051579-98, not patented, as the male, or pollen, parent. The new *Spathiphyllum* plant was discovered and selected by the Inventor as a single plant within the progeny of the stated cross-pollination in a controlled greenhouse environment in Naaldwijk, The Netherlands in December, 2013.

Asexual reproduction of the new *Spathiphyllum* plant by in vitro meristem culture in a controlled environment in Naaldwijk, The Netherlands since July, 2015 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spamalgro'. These characteristics in combination distinguish 'Spamalgro' as a new and distinct *Spathiphyllum* plant:

1. Large, upright, outwardly arching and uniform plant habit.
2. Freely clumping growth habit; bushy and dense plants.
3. Large glossy dark green-colored leaves.
4. Freely flowering habit.
5. Large white-colored spathes that are positioned between and above the foliar plane on strong and erect scapes.
6. Flowers that produce very little to no pollen.
7. Good inflorescence longevity.

Plants of the new *Spathiphyllum* differ from plants of the female parent selection in the following characteristics:

1. Plants of the new *Spathiphyllum* are shorter than plants of the female parent selection.
2. Plants of the new *Spathiphyllum* have higher quality inflorescences than plants of the female parent selection.

Plants of the new *Spathiphyllum* differ from plants of the male parent selection in the following characteristics:

1. Roots of plants of the new *Spathiphyllum* are stronger than roots of plants of the male parent selection.
2. Plants of the new *Spathiphyllum* are larger than plants of the male parent selection.

Plants of the new *Spathiphyllum* can also be compared to plants of *Spathiphyllum* Schott. 'Spagrodo', not patented. In side-by-side comparisons, plants of the new *Spathiphyllum* differ from plants of 'Spagrodo' in the following characteristics:

1. Plants of the new *Spathiphyllum* are faster growing than plants of 'Spagrodo'.
2. Plants of the new *Spathiphyllum* are more freely flowering than plants of 'Spagrodo'.
3. Scapes of plants of the new *Spathiphyllum* are longer than scapes of plants of 'Spagrodo'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet (FIG. 1 of 3) is a side perspective view of a typical plant of 'Spamalgro' grown in a container and is the same photograph as filed in the U.S. Provisional Patent application Ser. No. 62/918,087.

Figure 2:
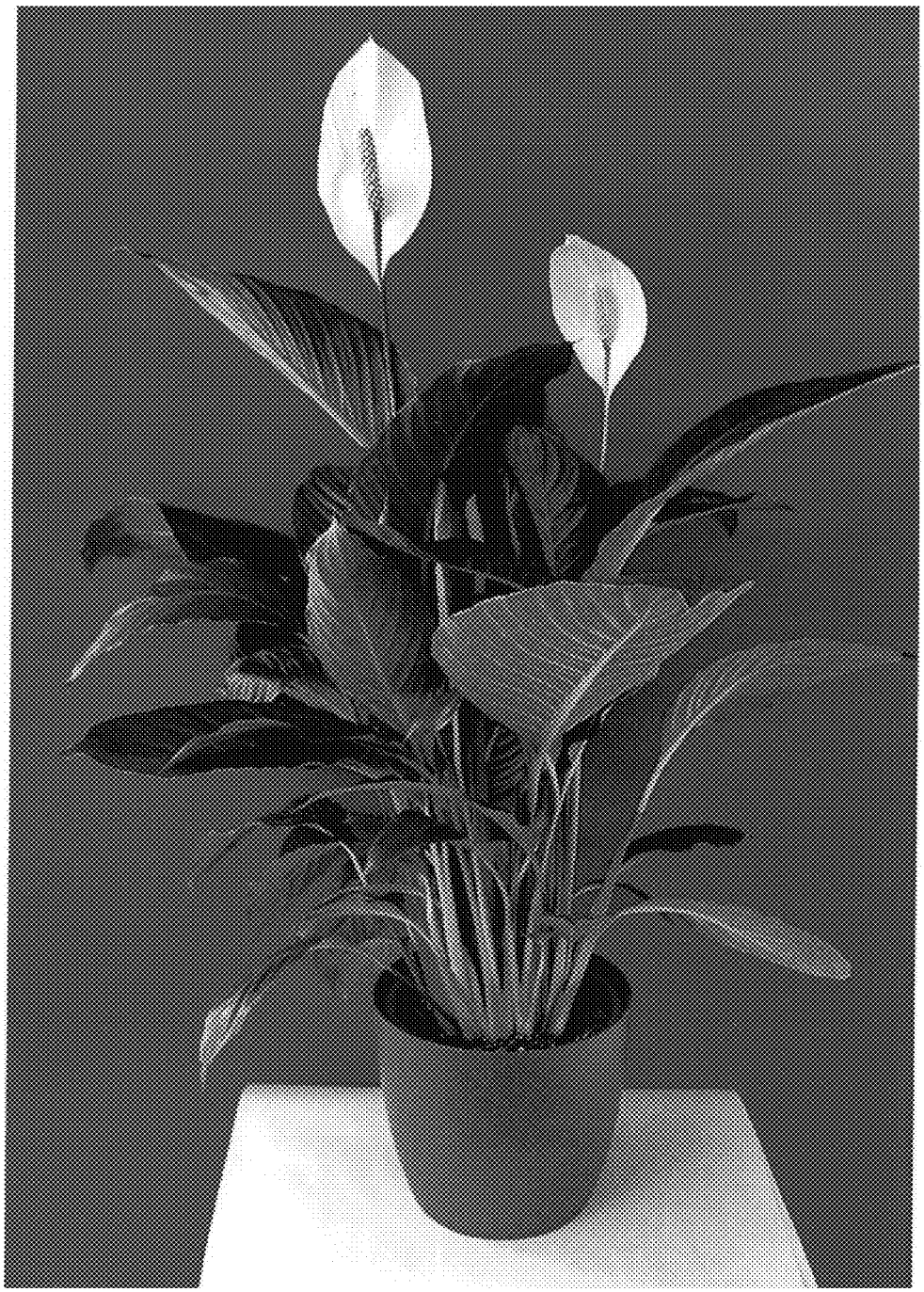

The photograph on the second sheet (FIG. 2 of 3) is a side perspective view of a typical plant of 'Spamalgro' grown in a container.

Figure 3:
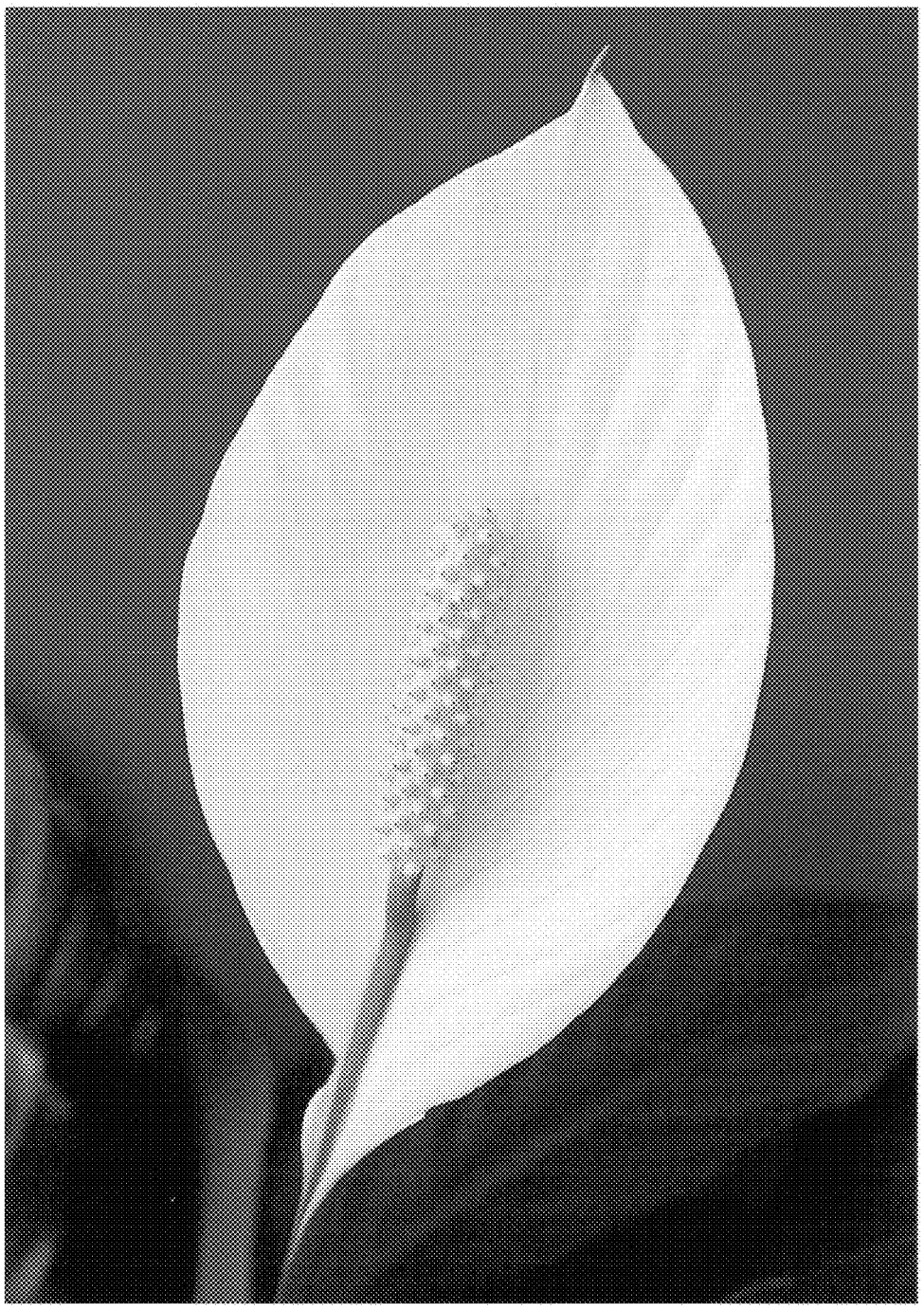

The photograph on the third sheet (FIG. 3 of 3) is a close-up view of a typical inflorescence of 'Spamalgro'.

DETAILED BOTANICAL DESCRIPTION

The aforementioned photographs and following observations and measurements describe plants grown during the autumn and winter in 19-cm containers in a glass-covered greenhouse in Naaldwijk, The Netherlands and under cultural practices typical of commercial *Spathiphyllum* production. During the production of the plants, day temperatures ranged from 19° C. to 30° C., night temperatures ranged from 19° C. to 24° C. and light levels averaged 5 klux. Plants were 42 weeks from transplanting rooted young plants when the photographs and the detailed description were taken. In the following description, color references are made to The Royal Horticultural Society Colour Chart, 2015 Edition, except where general terms of ordinary dictionary significance are used.

Botanical classification: *Spathiphyllum* Schott. 'Spamalgro'.

Parentage:

*Female, or seed, parent*.—Proprietary selection of *Spathiphyllum* Schott. identified as code number 20081932-45, not patented.

*Male, or pollen, parent*.—Proprietary selection of *Spathiphyllum* Schott. identified as code number 20051579-98, not patented.

Propagation:

*Type*.—By in vitro meristem culture.

*Time to initiate roots, summer*.—About twelve days at temperatures about 23° C.

*Time to initiate roots, winter*.—About 13 days at temperatures about 23° C.

*Time to produce a rooted young plant, summer*.—About 119 days at temperatures about 21° C.

*Time to produce a rooted young plant, winter*.—About 130 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Large, upright, outwardly arching and uniform plant habit; overall plant shape, broadly inverted triangle; vigorous growth habit and moderate to rapid growth rate.

*Clumping habit*.—Freely clumping habit, bushy and dense growth habit with about 14 clumps developing per plant.

*Plant height, from soil level to top of leaf plane*.—About 70.4 cm.

*Plant height, from soil level to top of inflorescences*.—About 80.5 cm.

*Plant diameter or spread*.—About 82 cm.

*Leaf description*.—Arrangement: Alternate; simple. Length: About 38.9 cm. Width: About 18.5 cm. Shape: Ovate to broadly ovate. Apex: Apiculate. Base: Attenuate. Margin: Entire; moderately undulate; not lobed. Texture and luster, upper surface: Smooth, glabrous; glossy. Texture and luster, lower surface: Smooth, glabrous; moderately glossy. Venation pattern: Pinnate. Color: Developing leaves, upper surface: Slightly darker than 143A. Developing leaves, lower surface: Close to between 138A and 138B. Fully expanded leaves, upper surface: Slightly darker than NN137A; venation, close to 144A. Fully expanded leaves, lower surface: Close to between 137B and 147B; venation, close to 144B to 144C. Petioles: Length (excluding geniculum): About 29.6 cm. Diameter, just below geniculum: About 5 mm. Diameter, at plant base: About 1.6 cm. Strength: Strong. Texture and luster, upper and lower surfaces: Smooth, glabrous; matte. Color, upper surface: Close to between 145D and 157B. Color, lower surface: Slightly darker than 143A. Geniculum length: About 4.7 cm. Geniculum diameter: About 6.5 mm. Geniculum texture and luster, upper and lower surfaces: Smooth, glabrous; slightly glossy. Geniculum color, upper and lower surfaces: Close to 144A. Wing length: About 25.1 cm. Wing diameter: About 1.25 cm. Wing color: Close to 143B; towards the margins, slightly darker than 143A.

Inflorescence description:

*Inflorescence arrangement and flowering habit*.—Moderately to strongly cupped erect spathes with columnar spadices held between and above the foliar plane on strong and erect scapes; flowering structures arise from leaf axils; plants begin flowering about six months after transplanting rooted young plants; freely and continuous flowering year-round under greenhouse conditions in The Netherlands; freely flowering habit, typically about six inflorescences developing per plant.

*Fragrance*.—Moderately fragrant; fragrance, sweet and pleasant.

*Inflorescence longevity*.—Inflorescences last more than three weeks on the plant; inflorescences persistent.

*Spathe*.—Length: About 18.6 cm. Width: About 8.6 cm. Depth: About 5 cm. Shape: Elliptic to slightly obovate. Apex: Apiculate; not twisted. Base: Attenuate. Margin: Entire; very slightly and coarsely undulate. Texture and luster, front surface: Smooth, glabrous; somewhat leathery; moderately glossy. Texture and luster, rear surface: Smooth, glabrous; somewhat leathery; glossy. Color: When developing, front surface: Close to NN155B; apex, close to 144A. When developing, rear surface: Close to NN155A to NN155B; apex and main vein, close to 144A. Fully developed, front surface: Close to NN155B; apex, close to 144C; main vein, lighter than 148D; color does not change with development. Fully developed, rear surface: Close to NN155B to NN155C; apex, close to 144C; main vein, close to 144B; color does not change with development.

*Spadix*.—Length: About 6.4 cm. Diameter: About 1.6 cm. Shape: Columnar; apex, obtuse; base, obtuse; cross-section, circular. Aspect: Close to erect, about 5° from scape axis. Color, immature: Close to 158C to 158D. Color, mature: Close to 158B. Flowers: Quantity per spadix: Numerous, about 220. Shape: Rounded. Height: About 3.5 mm. Diameter: About 5 mm. Anther color: Close to NN155A. Pollen amount: None to scarce. Pollen color: Close to 155C. Stigma color: Close to 155A. Ovary color: Close to 158D.

*Scapes*.—Length: About 66.2 cm. Diameter: About 5.5 mm. Strength: Strong. Aspect: About 15° from vertical. Texture and luster: Smooth, glabrous; matte. Color: Close to 143C.

*Seeds and fruits*.—To date, seed and fruit development have not been observed on plants of the new *Spathiphyllum*.

Pathogen & pest resistance: To date, plants of the new *Spathiphyllum* have not been observed to be resistant to pathogens or pests common to *Spathiphyllum* plants.

Temperature tolerance: Plants of the new *Spathiphyllum* have been observed to be tolerant to temperatures ranging from about 5° C. to about 40° C. and to be suitable for USDA Hardiness Zones 10 to 13.

It is claimed:

1. A new and distinct *Spathiphyllum* plant named 'Spamalgro' as illustrated and described.

* * * * *